United States Patent [19]

Wolter

[11] Patent Number: 5,414,093

[45] Date of Patent: May 9, 1995

[54] HYDROLYZABLE AND POLYMERIZABLE SILANES

[75] Inventor: Herbert Wolter, Gerchsheim, Germany

[73] Assignee: Fraunhofer-Gesellschaft zur Forderung der Angewandten, Munchen, Germany

[21] Appl. No.: 916,584

[22] Filed: Jul. 20, 1992

[30] Foreign Application Priority Data

Jul. 30, 1991 [DE] Germany .................. 41 25 201.2

[51] Int. Cl.⁶ ............................................. C07D 323/02
[52] U.S. Cl. ....................................... 549/214; 528/32; 528/40; 528/10
[58] Field of Search .......................................... 549/214

[56] References Cited

U.S. PATENT DOCUMENTS 4,410,354  10/1983  Sundelin et al. ............... 549/331
4,599,155   7/1986  Suzuki et al. .................. 528/27
4,935,413   6/1990  Urano et al. ................... 514/178

Primary Examiner—C. Warren Ivy
Assistant Examiner—Raymond Covington
Attorney, Agent, or Firm—Marshall & Melhorn

[57] ABSTRACT

Hydrolyzable and polymerizable silanes for producing poly (hetero) condensation products and (hetero) polymers, the silanes having the general formula (I)

$$Y_n \, Si \, X_m \, R_{4-(n+m)} \quad (I),$$

wherein the residues X, Y and R may be the same or different and are defined as follows:

R = alkyl, alkenyl, aryl, alkylaryl or arylalkyl,

X = hydrogen, halogen, hydroxyl, alkoxy, acyloxy, alkylcarbonyl, alkoxycarbonyl or $NR'_2$, with R' = hydrogen, alkyl or aryl, Y = a substituent containing a substituted or unsubstituted 1,4,6-trioxaspiro-[4,4]-nonane residue, n = 1, 2 or 3, m = 1, 2 or 3, with n+m ≦ 4.

The silanes of the present invention are processed to form scratch-resistant coatings, filling, adhesive or sealing compounds, molded articles or embedding media.

5 Claims, No Drawings

HYDROLYZABLE AND POLYMERIZABLE SILANES

The present invention relates to hydrolyzable and polymerizable silanes, a process for the production thereof, and the use thereof for producing silicic acid condensation polymers and heteropolycondensation polymers, and for producing polymers and heteropolymers.

Hydrolyzable organically modified silanes are widely used in the production of scratch-resistant coatings for widely differing substrates, and of fillers, adhesive and sealing compounds, or molded articles. For this-purpose these silanes are hydrolytically condensed, either by themselves or in mixtures or in presence of other hydrolyzable and/or condensable components, the final curing being made thermally or photochemically.

Scratch-resistant coatings known from DE 34 07 087 C2, for example, are formed by hydrolytic condensation of a mixture which may consist of a hydrolyzable titanium- or zincorganic compound $MR_4$ and a hydrolyzable silane $R'_m(R''Y)_n SiX_{(4-m-n)}$ having functional organic groups, wherein R represents, for example, halogen, hydroxyl, alkoxy or acyloxy, R' represents, for example, alkyl or alkenyl, R" represents, for example, alkylene or alkenylene, and X represents a hydrolyzable residue.

Adhesive and sealing compounds known from DE 35 36 716 A1, for example, were obtained by hydrolytic condensation of one or more organosilanes of the general formula $R_m SiX_{4-m}$ and optionally one or more of the components $SiX_4$ and/or $R_n(R''Y)_p SiX_{4-n-p}$, wherein R and R" represent, for example, alkyl, alkenyl, aryl, alkylaryl, arylalkyl, alkenylaryl or arylalkenyl, X represents, for example, hydrogen, halogen, hydroxyl, alkoxy or acyloxy, and Y represents, for example, a halogen or an optionally substituted amino, amide, aldehyde, alkylcarbonyl, carboxyl, hydroxyl, mercapto or cyano group.

Furthermore, commercially available silanes having reactive double bonds are known, such as (meth)acryloxysilane of the following type

wherein R represents hydrogen or methyl, and X is, for example, halogen or alkoxy. These silanes are hydrolyzable and polymerizable and can be used for the production of the above-described systems. They offer the great advantage that the resulting coating, filler, adhesive or sealing compound, or molded article may be thermally or photochemically cured at the positions of the reactive double bonds.

However, in all of these systems disadvantages arise from the fact that during polymerization a decrease of volume, i.e. a so-called curing-shrinkage occurs, leading to stresses within the coating, filler, adhesive or sealing compound, or molded articles, and/or to a loss of gauge uniformity. The stresses may lead to macroscopic damage, i.e. crack formation or even blistering, or to microscopic damage such as optical defects (dependency of refractive index on location, interference), reduced mechanical stability, surface structures, etc. The loss of gauge uniformity is very troublesome, particularly in the case of molding compounds (optical gratings, etc.) and molded articles (e.g. during injection molding, etc.).

It was therefore the object of the present invention to provide novel organically modified silanes which are hydrolyzable and polymerizable and which, by themselves or in mixtures, or together with other hydrolyzable, condensable or polymerizable components, may be processed to produce scratch-resistant coatings, fillers, adhesive or sealing compounds, molded articles or embedding media that undergo no decrease of volume during curing and adhere well to the substrate. These silanes are intended to be universally usable when no shrinkage, or as little shrinkage as possible, or even an expansion is desired, and they must be capable of being introduced by synthesis into an inorganic-organic composite structure, i.e. an inorganic-organic network. Furthermore, it is intended that these silanes be capable of being prepared rapidly and easily, i.e. without any elaborate processes of synthesis.

This object is achieved by hydrolysable and polymerizable silanes of the general formula (I)

$$Y_n SiX_m R_{4-(n+m)} \qquad (I),$$

wherein the residues X, Y and R may be the same or different and are defined as follows:

R=alkyl, alkenyl, aryl, alkylaryl or arylalkyl,
X=hydrogen, halogen, hydroxyl, alkoxy, acyloxy, alkylcarbonyl, alkoxycarbonyl or $NR'_2$, with R'=hydrogen, alkyl or aryl,
Y=a substituent containing a substituted or unsubstituted 1,4,6-trioxaspiro-[4,4]-nonane residue,
n=1, 2 or 3,
m=1, 2 or 3, with n+m≦4.

The residues X are hydrolyzable and the residues Y are polymerizable, wherein in each case at least one of the residues X and Y as defined above is present in the silanes of the present invention.

The alkyl residues are, for example, straight chain, branched chain, or cyclic residues having 1 to 20, preferably 1 to 10 carbon atoms, and particularly preferred are lower alkyl residues having 1 to 6 carbon atoms. Specific examples are methyl, ethyl, n-propyl, i-propyl, n-butyl, s-butyl, t-butyl, i-butyl, n-pentyl, n-hexyl, cyclohexyl, 2-ethylhexyl, dodecyl and octadecyl.

The alkenyl residues are, for example, straight chain, branched chain or cyclic residues having 2 to 20, preferably 2 to 10 carbon atoms, and particularly preferred are lower alkenyl residues having 2 to 6 carbon atoms, e.g. vinyl, allyl or 2-butenyl.

Preferred aryl residues are phenyl, biphenyl and naphthyl. The alkoxy, acyloxy, alkylcarbonyl, alkoxycarbonyl and amino residues are derived preferably from the above-named alkyl and aryl residues. Specific examples are methoxy, ethoxy, n- and i-propoxy, n-, i-, s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The named residues may optionally carry one or more substituents, e.g. halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxyl, formyl, carboxyl, mercapto, cyano, isocyanato, nitro, epoxy, $SO_3H$ and $PO_4H_2$. Of the halogens, fluorine, chlorine and bromine are preferred.

The substituted or unsubstituted 1,4,6-trioxaspiro-[4,4]-nonane groups are linked to the Si atom through alkylene or alkenylene residues that may contain interposed ether or ester groups. Specific examples and preferred embodiments of the residues Y are

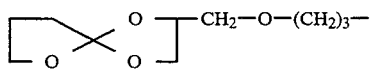

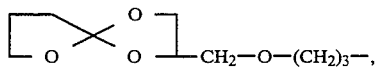

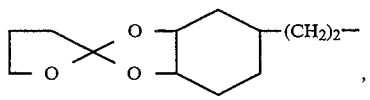

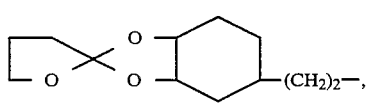

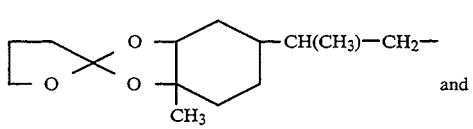

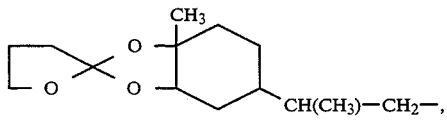

wherein the ring system derived from γ-butyrolactone may be substituted, as is also illustrated in claim 2. The substituents may be hydrogen, halogen, hydroxyl, alkyl, alkenyl, aryl, alkylaryl, arylalkyl, alkylcarbonyl, alkoxycarbonyl, acryloxy or methacryloxy groups. Concrete examples of this are

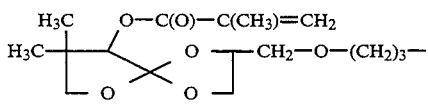

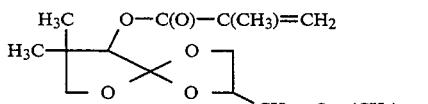

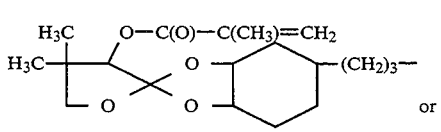

or

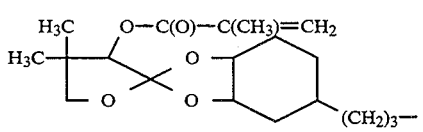

Concrete examples of silanes of the present invention are

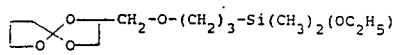

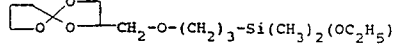

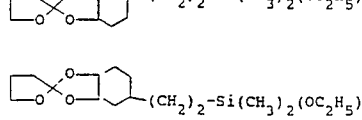

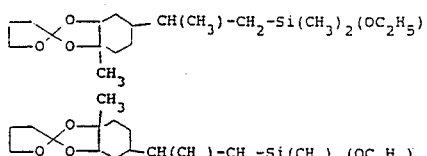

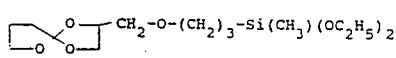

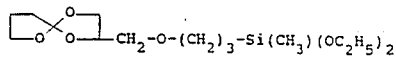

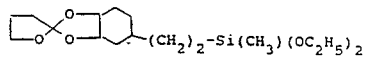

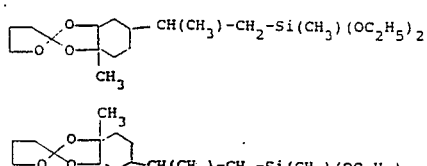

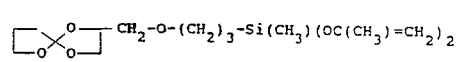

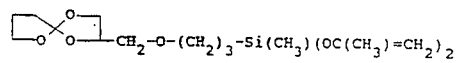

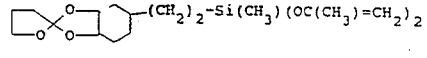

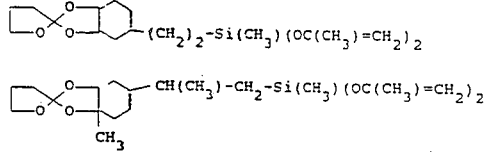

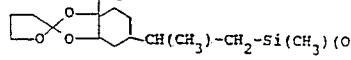

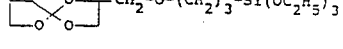

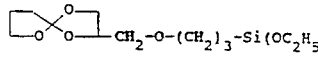

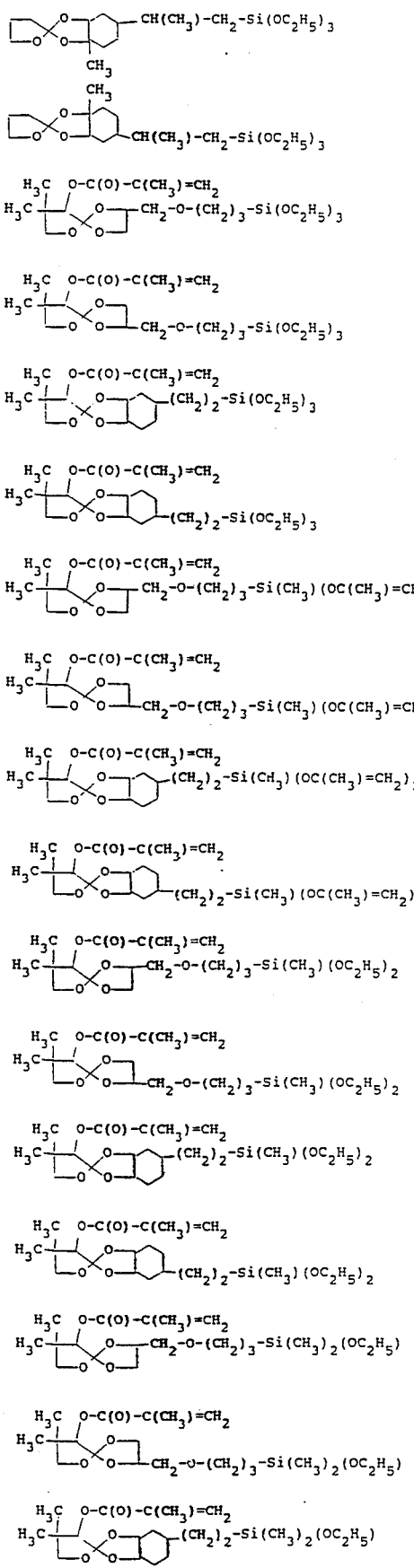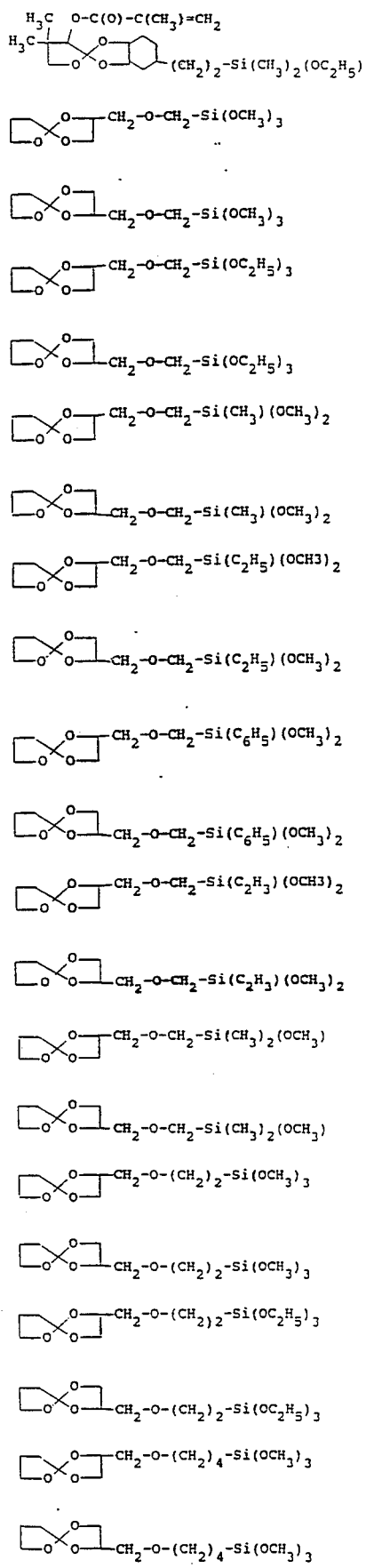

-continued

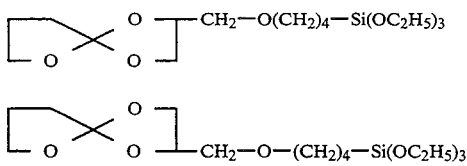

The silanes of the present invention are produced by reacting silanes of the general formula (II)

$$Y'_n SiX_m R_{4-(n+m)} \tag{II},$$

with substituted or unsubstituted γ-butyrolactones in presence of a Lewis acid and optionally in an inert solvent free from water, wherein the γ-butyrolactone is added in excess. The residues X, Y' and R of the general formula (II) may be the same or different, X, R, n and m have the same meanings as for the silanes of the present invention as represented by the general formula (i), and Y' is a residue representing a substituted oxirane ring. Concerning any possible modifications of the residues X and R, the same applies as has been stated in the case of the silanes of the present invention represented by the general formula (I).

Specific examples of silanes of the general formula (II) are: glycidoxymethyl trimethoxysilane, glycidoxymethyl triethoxysilane, 2-glycidoxyethyl trimethoxysilane, 2-glycidoxyethyl triethoxysilane, 3-glycidoxypropyl trimethoxysilane, 3-glycidoxypropyl triethoxysilane, 3-glycidoxypropyl tri(methoxyethoxy)silane, 3-glycidoxypropyl triacetoxysilane, 4-glycidoxybutyl trimethoxysilane, 4-glycidoxybutyl triethoxysilane, glycidoxymethyl (methyl)dimethoxysilane, glycidoxymethyl (ethyl)dimethoxysilane, glycidoxymethyl (phenyl)dimethoxysilane, glycidoxymethyl (vinyl)-dimethoxysilane, glycidoxymethyl (dimethyl)methoxysilane, 2-glycidoxyethyl (methyl)dimethoxysilane, 2-glycidoxyethyl (ethyl)dimethoxysilane, 2-glycidoxyethyl (dimethyl)methoxysilane, 3-glycidoxypropyl (methyl)dimethoxysilane, 3-glycidoxypropyl (ethyl)-dimethoxysilane, 3-glycidoxypropyl (dimethyl)methoxysilane, 4-glycidoxybutyl (methyl)dimethoxysilane, 4-glycidoxybutyl (ethyl)dimethoxysilane, 4-glycidoxybutyl (dimethyl)methoxysilane, bis-(glycidoxymethyl) dimethoxysilane, bis-(glycidoxymethyl) diethoxysilane, bis-(glycidoxyethyl) dimethoxysilane, bis-(glycidoxyethyl) diethoxysilane, bis-(glycidoxypropyl) dimethoxysilane, bis-(glycidoxypropyl) diethoxysilane, tris-(glycidoxymethyl) methoxysilane, tris-(glycidoxymethyl) ethoxysilane, tris-(glycidoxyethyl) methoxysilane, tris-(glycidoxyethyl) ethoxysilane, tris-(glycidoxypropyl) methoxysilane, tris-(glycidoxypropyl) ethoxysilane, glycidylmethyl trimethoxysilane, glycidylmethyl triethoxysilane, 2-glycidylethyl trimethoxysilane, 2-glycidylethyl triethoxysilane, 3-glycidylpropyl trimethoxysilane, 3-glycidylpropyl triethoxysilane, 3-glycidylpropyl tri(methoxyethoxy) silane, 3-glycidylpropyl triacetoxysilane, 3.4-epoxycyclohexylmethyl trimethoxysilane, 3.4-epoxycyclohexylmethyl triethoxysilane, 3.4-epoxycyclohexylethyl trimethoxysilane, 3.4-epoxycyclohexylpropyl trimethoxysilane, 3.4-epoxycyclohexylbutyl trimethoxysilane.

Silanes of the general formula (II) are commercially available, thus for example, 3-glycidoxypropyl dimethylethoxysilane, (3-glycidoxypropyl) methyldiethoxysilane, 3-glycidoxypropyl methyl-di-isopropeneoxysilane, (3-glycidoxypropyl) trimethoxysilane, 2-(3.4-epoxycyclohexyl) ethyltrimethoxysilane or [2-(3.4-epoxy-4-methylcyclohexyl)propyl] methyldiethoxysilane, from ABCR GmbH & Co. KG (Karlsruhe).

All of these silanes can be converted with γ-butyrolactones into the corresponding spiro-silanes of the present invention.

Suitable γ-butyrolactones for producing the spiro-silanes of the present invention are the unsubstituted γ-butyrolactone as well as γ-butyrolactones substituted with halogen, hydroxyl, alkyl, alkenyl, aryl, alkylaryl, arylalkyl, alkylcarbonyl, alkoxycarbonyl, acryloxy or methacryloxy groups.

The alkyl residues are, for example, straight chain, branched chain or cyclic residues having 1 to 10 carbon atoms, the lower alkyl residues having 1 to 6 carbon atoms being especially preferred. Specific examples are methyl, ethyl, n-propyl, i-propyl, n-butyl, s-butyl, t-butyl, i-butyl, n-pentyl, n-hexyl.

The alkenyl residues are, for example, straight chain, branched chain or cyclic residues having 2 to 10 carbon atoms, especially preferred are lower alkenyl residues having 2 to 6 carbon atoms, such as vinyl, allyl or 2-butenyl.

Specific examples and preferred embodiments of Lewis acids are, for example, $BF_3 \cdot Et_2O$, $SnCl_4$ or $AlCl_3$.

The conversion of the silanes of the general formula (II) with the γ-butyrolactones into the spiro-silanes of the present invention is effected with exclusion of water, optionally in an inert solvent. The spiro-silanes of the present invention are purified using known techniques, for example, high-vacuum distillation.

The preparation of the spiro-silanes of the present invention will be schematically illustrated using as an example the reaction of γ-butyrolactone with (3-glycidoxypropyl) trimethoxysilane.

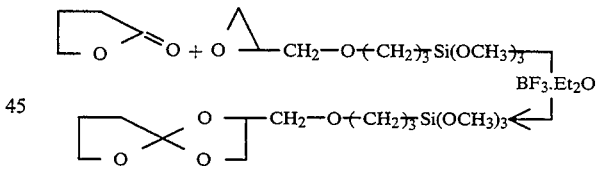

It is also possible to modify further the spiro-silanes obtained according to the above reaction using known methods and to introduce other substitutents, for example into the ring system derived from γ-butyrolactone. Thus, it is described in Journal f. prakt. Chemie, Volume 330, No. 2, 1988, pages 316-318, how methacryl groups can be introduced into spiro-cyclic ortho-esters at this ring system.

The spiro-silanes of the present invention are stable compounds and may be processed either by themselves, or together with other hydrolyzable condensable and-/or polymerizable components, to produce silicic acid condensation polymers or silicic acid heteropolycondensation polymers which are then finally cured by polymerization with ring-opening of the 1,4,6-trioxaspiro-[4,4]-nonane group. However, the silanes of the present invention may also be processed by themselves, or together with other hydrolyzable condensable and-/or polymerizable components, to produce polymers that may be consolidated by subsequent hydrolytic condensation.

Silicic acid (hetero)polycondensates modified with organic groups, as well as methods for the preparation thereof (e.g. starting from hydrolytically condensable organo-silanes using the sol-gel-method) are known in large numbers. Condensation products of this kind are used for widely differing purposes, for example as molding compounds, varnishes for coatings, etc. However, because of the various possibilities of application of this class of substances, there is also a constant need for modification of the already known condensation products, in order to open up new fields of application, on the one hand, and to optimize their properties for certain uses, on the other hand.

The spiro-silanes of the present invention are hydrolyzable and condensable in a basic environment, without the spiro-complex being prematurely opened. This makes it possible to introduce the spiro-silanes of the present invention into an inorganic-organic lattice in a synthesis by means of hydrolytic condensation. The spiro-silanes of the present invention contain hydrolyzable groups X, for example alkoxy groups, so that they can be used to synthesize an inorganic network (Si—O—Si-units), whilst the spiro groups contained in the residue Y can be polymerized whilst synthesizing an organic network. This makes it possible to replace organically modified hydrolyzable and condensable silanes in coating, filling, adhesive and sealing compounds, molded articles and embedding media, as known in prior art, by the spiro-silanes of the present invention.

In order to synthesize the inorganic network, the silanes of the present invention are hydrolyzed and polycondensed, with optional addition of other co-condensable components. The polycondensation is performed preferably according to the sol-gel-method, as described for example in DE-A1 27 58 414, 27 58 415, 30 11 761, 38 26 715 and 38 35 968.

In order to synthesize the organic network, the spiro-silanes of the present invention are polymerized, optionally with addition of other copolymerizable components. For example, the polymerization may be performed thermally or photochemically, using methods as described in DE-A1 31 43 820, 38 26 715 and 38 35 968.

Compounds are capable of being subjected to radical and/or ion polymerization may be added as the further polymerizable components. Compounds that may be subjected to radical polymerization and can be added are, for example, those with C=C double bonds, e.g. acrylates or methacrylates, wherein polymerization occurs through the C=C double bonds. Ion polymerizable compounds that may be added contain, for example, ring systems capable of being subjected to cationic polymerization with ring-opening, such as spiro-ortho-esters, spiro-orthocarbonates, bicyclic spiro-ortho-esters, mono or oligo epoxides, or vinylethers. However, compounds may also be added which can be subjected to cationic as well as radical polymerization, e.g. methacryloyl-spiro-ortho-esters. These undergo radical polymerization through the C=C double bond and cationic polymerization with ring-opening. The preparation of these systems is described, for example, in Journal f. prakt. Chemie, Volume 330, No. 2, 1988, pages 316–318.

Furthermore, it is possible to add other known silane-linked cyclic systems capable of being copolymerized. Such systems are those, for example, which contain epoxides and are used, amongst other purposes, for producing the spiro-silanes of the present invention. Such systems are described together with the production of the spiro-silanes of the present invention.

The spiro-silanes of the present invention represent highly reactive systems leading to poly(hetero)condensation products capable of yielding mechanically stable coatings or molding and filler materials within short time, for example under UV radiation. The spiro-silanes of the present invention may be produced by simple addition reactions and may contain a variable number of reactive groups of differing functionality according to suitable choice of the starting compounds.

The synthesis of a three-dimensional organic network is possible in the presence of two or more residues Y. The mechanical properties (e.g. flexibility) and the physical-chemical properties (adsorption, refractive index, adhesion etc.) of the poly(hetero)condensation products can be influenced by the distance between the Si atom and the spiro-group, i.e. by the chain length, and by the presence of further functional groups in this chain, as well as by the number of alkoxy groups on the silane. By synthesizing an inorganic network, silicone or glass-like properties of the poly(hetero)condensation products may be obtained according to the kind and number of hydrolyzable groups (e.g. alkoxy groups).

If, in addition, the possibilities of varying the co-condensable and copolymerizable components are taken into consideration, it becomes evident that the spiro-silanes of the present invention make it possible to provide silicic acid poly(hetero)condensation products suitable of being adapted in manifold manner to given fields of application. They may therefore find use in all fields in which silicic acid (hetero)polycondensation products are already being employed, but they can also open up new possibilities of use, for example in the field of optics, electronics, medicine, opto-electronics and packing materials for foods, etc.

The spiro-silanes of the present invention may be used either as they are, or in compositions containing additives adapted to the purpose of utilization, e.g. usual varnish additives, solvents, fillers, photo-initiators, thermal initiators, flow improvers and pigments. The spiro-silanes of the present invention, or the silane-containing compositions, are suitable, for example, for the manufacture of coating, filler or bulk materials, adhesives and injection molding compositions, fibers, thin sheets, adhesion promoters, molding compounds and embedding media. Because of the presence of the spiro-groups, they undergo no shrinkage, or only small shrinkage, or even, if desired, an expansion during curing. The shrinkage thus may be adapted to the given conditions of the application concerned. Coatings and molded articles made from the spiro-silanes of the present invention possess the advantage that they may be photochemically provided with a structure. Specific fields of application, for example, are those of applying coatings to substrates of metal, plastics, paper, ceramics etc. by immersion, pouring, brushing, spraying, electrostatic spraying, electro-dip coating etc., the application to optical, opto-electrical or electronic components, the manufacture of fillers, the manufacture of scratch-resistant and abrasion-resistant corrosion protective coatings, the manufacture of molded articles, for example by injection molding, casting or extrusion, and the manufacture of composites, for example with fibers, fillers or fabrics.

In addition to the spiro-silanes of the present invention having the formula (I), further hydrolytically condensable compounds of silicon, boron, aluminium, phosphorus, tin, lead, transition metals, lanthanides or actinides may be used. These compounds may be used either as such or in an already pre-condensed form for producing the condensation polymers. Preferably at least 10 mole-%, in particular at least 80 mole-%, and especially at least 90 mole-%, based on the monomeric compounds, of the starting materials for producing the silicic acid (hetero)polycondensation products are silicon compounds.

It is also preferred that the silicic acid (hetero)polycondensation products are based on at least 5 mole-%, for example 25 to 100 mole-%, in particular 50 to 100 mole-% and specifically 75 to 100 mole-%, based on the monomeric compounds, of one or more of the spiro-silanes of the present invention.

Of the various hydrolytically condensable silicon compounds differing from the silanes of the general formula (III), but which are optionally usable, those of the general formula (III) are especially preferred, $$R_a(R''Z')_b SiX_{4-(a+b)} \quad (III),$$

wherein the residues R, R", X and Z' may be the same or different and are defined as follows:

R = alkyl, alkenyl, aryl, alkylaryl or arylalkyl,

R" = alkylene or alkenylene, wherein these residues may contain interposed oxygen or sulphur atoms or —NH— groups, X = hydrogen, halogen, hydroxyl, alkoxy, acyloxy, alkyl carbonyl, alkoxycarbonyl or $NR'_2$, with R' = hydrogen, alkyl or aryl, Z' = halogen or an optionally substituted amino, amide, aldehyde, aklylcarbonyl, carboxyl, mercapto, cyano, alkoxy, alkoxycarbonyl, sulfonic acid, phosphoric acid, acryloxy, methacryloxy, epoxy or vinyl group, a = 0, 1, 2 or 3, b = 0, 1, 2 or 3, with a+b = 1, 2 or 3.

Silanes of this kind are described, for example, in DE 34 07 087 C2. The alkyl residues may be, for example, straight chain, branched chain or cyclic residues having 1 to 20, preferably 1 to 10 carbon atoms. Especially preferred are lower alkyl residues having 1 to 6 carbon atoms. Specific examples are methyl, ethyl, n-propyl, i-propyl, n-butyl, s-butyl, t-butyl, i-butyl, n-pentyl, n-hexyl, cyclohexyl, 2-ethylhexyl, dodecyl and octadecyl.

The alkenyl residues are, for example, straight chain, branched chain or cyclic residues having 2 to 20, preferably 2 to 10 carbon atoms. Especially preferred are lower alkenyl residues having 2 to 6 carbon atoms, such as vinyl, allyl or 2-butenyl.

Preferred aryl residues are phenyl, biphenyl and naphthyl.

The alkoxy, acyloxy, alkylcarbonyl, alkoxycarbonyl and amino residues are preferably derived from the above-named alkyl and aryl residues. Specific examples are methoxy, ethoxy, n- and i-propoxy, n-, i-, s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The named residues may optionally carry one or more substituents, for example halogen, alkyl, hydroxylalkyl, alkoxy, aryl, aryloxy, alkylcarbonyl, alkoxycarbonyl, furfuryl, tetrahydrofurfuryl, amino,i alkylamino, isocyanato, dialkylamino, trialkylammonium, amido, hydroxyl, formyl, carboxyl, mercapto, cyano, nitro, epoxy, $SO_3H$ and $PO_4H_2$.

Of the halogens, fluorine, chlorine and bromine are preferred.

Specific examples of hydrolytically condensable silanes of the general formula (III) are:

$CH_3$—Si—$Cl_3$, $CH_3$—Si—$(OC_2H_5)_3$, $C_2H_5$—Si—$Cl_3$, $C_2H_5$—Si—$(OC_2H_5)_3$, $CH_2$=CH—Si—$(OC_2H_5)_3$, $CH_2$=CH—Si—$(OC_2H_4OCH_3)_3$, $(CH_3)_2$—Si—$Cl_2$, $CH_2$=CH—Si—$(OOCCH_3)_3$, $(CH_3)_2$—Si—$(OC_2H_5)_2$, $(C_2H_5)_3$—Si—Cl, $(C_2H_5)_2$—Si—$(OC_2H_5)_2$, $(CH_3)_2(CH_2$=CH)—Si—$Cl_2$, $(CH_3)_3$—Si—Cl, (t-$C_4H_9$) $(CH_3)_2$—Si—Cl, $(CH_3O)_3$—Si—$C_3H_6$—NH—$C_2H_4$—NH—$C_2H_4$—$NH_2$, $(CH_3O)_3$—Si—$C_3H_6$—SH, $(CH_3O)_3$—Si—$C_3H_6$—NH—$C_2H_4$—$NH_2$, $(CH_3O)_3$—Si—$C_3H_6$—Cl, $(CH_3O)_3$—Si—$C_3H_6$—O—C(O)—C($CH_3$)=$CH_2$, $(CH_3)_2(CH_2$=CH—$CH_2$)—Si—Cl, $(C_2H_5O)_3$—Si—$C_3H_6$—$NH_2$, $(C_2H_5O)_3$—Si—$C_3H_6$—CN,

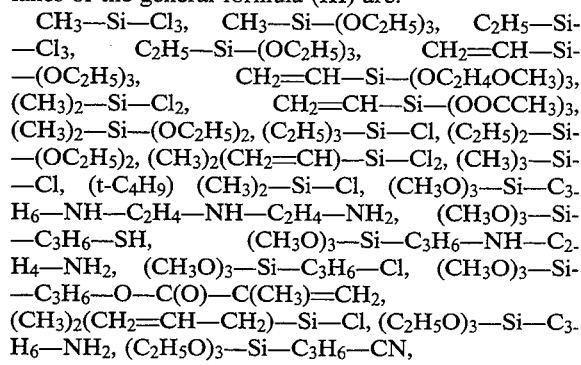

Of the hydrolytically condensable silicon compounds that differ from the silanes of the general formula (I) and may optionally be used, those of the general formula (IV) are also preferred, $$\{X_n R_k Si[R^2(A)_l]_{4-(n+k)}\}_x B \quad (IV),$$

wherein the residues A, R, $R^2$ and X may be the same or different and are defined as follows:

A = O, S, PR', POR', NHC(O)O or NHC(O)NR', with R' = hydrogen, alkyl or aryl,

B = a straight chain or branched chain organic residue derived from a compound B' having at least one (for l = 1 and A = NHC(O)O or NHC(O)NR'), or at least two C=C double bonds and 5 to 10 carbon atoms, with R' = hydrogen, alkyl or aryl, R = alkyl, alkenyl, aryl, alkylaryl or arylalkyl, $R^2$ = alkylene, arylene or alkylene-arylene, X = hydrogen, halogen, hydroxyl, alkoxy, acyloxy, alkyl carbonyl, alkoxycarbonyl or $NR'_2$, with R' = hydrogen, alkyl or aryl, n = 1, 2 or 3, k = 0, 1 or 2, l = 0 or 1, x = an integer, the maximum value of which corresponds to the number of double bonds in the compound B' minus 1, or is equal to the number of double bonds in the compound B', when l = 1 and A represents NHC(O)O or NHC (O) NR'.

Silanes of this kind have been described in DE 40 11 044 and in EP 091 105 355.

The alkyl residues are, for example, straight chain, branched chain or cyclic residues having 1 to 20, preferably 1 to 10 carbon atoms, and particularly preferred are lower alkyl residues having 1 to 6 carbon atoms. Specific examples are methyl, ethyl, n-propyl, i-propyl, n-butyl, s-butyl, t-butyl, i-butyl, n-pentyl, n-hexyl, cyclohexyl, 2-ethylhexyl, docecyl and octadecyl.

The alkenyl residues are, for example, straight chain, branched chain or cyclic residues having 2 to 20, preferably 2 to 20 carbon atoms, and especially preferred are lower alkenyl residues having 2 to 6 carbon atoms, such as vinyl, allyl or 2-butenyl.

Preferred aryl residues are phenyl, biphenyl and naphthyl.

The alkoxy, acyloxy, alkylcarbonyl, alkoxycarbonyl and amino residues are preferably derived from the above-named alkyl and aryl residues. Specific examples are methoxy, ethoxy, n- and i-propoxy, n-, i-, s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The named residues may optionally carry one or more substituents, for example, halogen, alkyl, hydroxylalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxyl, formyl, carboxyl, mercapto, cyano, isocyanato, nitro, epoxy, $SO_3H$ and $PO_4H_2$.

Of the halogens, fluorine, chlorine and bromine are preferred.

The residue B is derived from a substituted or unsubstituted compound B' having at least two C=C double bonds, for example, vinyl, allyl, acryl and/or methacrylate groups, and 5 to 50, preferably 6 to 30 carbon atoms. Preferably B is derived from a substituted or unsubstituted compound B' having two or more acrylate or methacrylate groups (such compounds are referred to hereunder as (meth)acrylates).

In case the compound B' is substituted, the substituents may be selected from the above-named substituents.

It is not absolutely necessary to isolate separately the spiro-silanes of the present invention for the further processing to produce the poly(hetero)condensation products. It is also possible, using a single-vessel-method, to produce the silanes first, and then, optionally after the addition of further hydrolyzable compounds, to condense the silanes hydrolytically.

Those of the optionally usable hydrolyzable aluminium compounds having the general formula (V) are particularly preferred, $$AlR°_3 \quad (V),$$

wherein the residues R° that may be the same or different are selected from halogen, alkoxy, alkoxycarbonyl and hydroxyl. Regarding more detailed (preferred) definitions of these residues, attention is drawn to the explanations given in connection with the suitable hydrolyzable silicon compounds. The last-named groups may also be wholly or partially replaced by chelate ligands (e.g. acetylacetone or acetoacetic ester, acetic acid).

Especially preferred aluminium compounds are the aluminium alkoxides and halides. In this connection, the following are mentioned as concrete examples $Al(OCH_3)_3$, $Al(OC_2H_5)_3$, $Al(O-n-C_3H_7)_3$, $Al(O-i-C_3H_7)_3$, $Al(OC_4H_9)_3$, $Al(O-i-C_4H_9)_3$, $Al(O-s-C_4H_9)_3$, $AlCl_3$, $AlCl(OH)_2$.

Compounds that are liquid at room temperature, such as aluminium-sec-butyrate and aluminium-isopropylate, are particularly preferred.

Suitable optionally usable hydrolyzable titanium or zirconium compounds are those of the general formula (VI), $$M X_y R_z \quad (VI),$$

wherein M represents Ti or Zr, y is an integer of 1 to 4, in particular 2 to 4, z represents 0, 1, 2 or 3, preferably 0, 1 or 2, and X and R are as defined in the case of the general formula (I). This also applies for the preferred definitions. Those of the compounds of the formula (VI) are especially preferred, wherein y is 4.

As in the case of the above Al compounds, complex Ti or Zr compounds may also be used. In this case, additionally preferred complexing agents are acrylic acid and methacrylic acid.

Concrete examples of usable Zr and Ti compounds are as follows:

$TiCl_4$, $Ti(OC_2H_5)_4$, $Ti(OC_3H_7)_4$, $Ti(O-i-C_3H_7)_4$, $Ti(OC_4H_9)_4$, $Ti(2-ethylhexoxy)_4$, $ZrCl_4$, $Zr(OC_2H_5)_4$, $Zr(OC_3H_7)_4$, $Zr(O-i-C_3H_7)_4$, $Zr(OC_4H_9)_4$, $Zr(2-ethylhexoxy)_4$, $ZrOCl_2$.

Further hydrolyzable compounds that may be used for producing the poly(hetero)condensation products are, for example, boron trihalides and boric acid esters, e.g. $BCl_3$, $B(OCH_3)_3$ and $B(OC_2H_5)_3$, tin tetrahalides and tin tetraalkoxides, e.g. $SnCl_4$ and $Sn(OCH_3)_4$, and vanadyl compounds, e.g. $VOCl_3$ and $VO(OCH_3)_3$.

As already mentioned, the production of the poly(hetero)condensation products can be made in a manner usual in this field. When, in practice, silicon compounds are exclusively used, the hydrolytic condensation may be effected in most cases by adding the required water at room temperature or with slight cooling directly (preferably with stirring and in presence of a hydrolysis and condensation catalyst) to the silicon compounds to be hydrolysed which may be present either as such or dissolved in a suitable solvent, and thereupon stirring the resulting mixture for some time (from one to several hours).

In presence of the reactive compounds of Al, Ti or Zr, it is recommendable, as a rule, to add the water stepwise. Without being dependent upon the reactivity of the compounds present, the hydrolysis normally occurs at temperatures between $-20°$ and $130°$ C., preferably between $0°$ and $30°$ C. or the boiling point of the optionally used solvent. As already indicated, the best manner of adding water depends, above all, upon the reactivity of the starting compounds used. Thus, the dissolved starting compounds may be added dropwise slowly into an excess of water, or water may be added as one portion or in portions to the optionally dissolved starting materials. It may also be expedient not to add the water as such, but to introduce it into the reaction system by means of water-containing organic or inorganic systems. In many cases it has been found especially suitable to introduce the amount of water into the reaction mixture by means of moisture-loaded adsorbents, e.g. molecular sieves, and of water-containing organic solvents, e.g. 80% ethanol. However, the addition of water may also be made by means of a chemical reaction wherein water is set free in the course of the reaction. Examples of this are esterifications.

If a solvent is to be used, it may be chosen not only from the lower aliphatic alcohols (e.g. ethanol or i-propanol), but also from ketones, preferably lower dialkyl ketones such as acetone or methylisobutyl ketone, ethers, preferably lower dialkyl ethers such as diethyl ether or dibutyl ether, THF, amides, esters, in particular ethyl acetate, dimethyl formamide, amines, in particular triethylamine, and mixtures thereof.

Preferably the hydrolysisis effected in an environment that is basic with respect to the spiro-silanes. This is created either with a basic solvent such as triethylamine, or by addition of basic hydrolysis and condensation catalysts such as $NH_3$, NaOH, KOH, methyl imidazole etc.

It is not necessary for all of the starting compounds to be present at the beginning of the hydrolysis (polycondensation); instead of this, in certain cases it may even be of advantage if only a portion of these compounds is first contacted with water, and the remaining compounds are added later.

In order to avoid, as far as possible, precipitation from occurring during the hydrolysis and the polycondensation, in particular when using hydrolyzable compounds different from silicon compounds, the addition of water may be effected in several stages, for example in three stages. Thus, in the first stage, for example, one tenth to one twentieth of the amount of water needed for hydrolysis may be added. After brief stirring, the addition of one fifth to one tenth of the necessary amount of water may be made, and finally the remainder may be added after further brief stirring.

The condensation time is determined by the starting components and their amounts, the catalyst that may be present, the reaction temperature, etc. The polycondensation generally takes place under normal pressure, however, it may also be effected at increased or reduced pressure.

The thus obtained poly(hetero)condensation product may be further processed either as such, or following a partial or almost complete removal of the solvent used. In some cases it may be of advantage to replace the excess water and the formed water and any optionally used additional solvent in the product obtained after the polycondensation by another solvent in order to stabilize the poly(hetero)condensation product. For this purpose, the reaction mixture may be thickened, for example in vacuum and with slightly increased temperature, to the extent that it may still be taken up without difficulty by another solvent.

In case these poly(hetero)condensation products are intended for use as varnishes for coating (for example plastics such as PVC, PC, PMMA, PE, PS, etc., glass, paper, wood, ceramics, metal etc.), usual varnish additives such as coloring agents (pigments or dyes), fillers, oxidation inhibitors, flow improvers, UV absorbers, stabilizers or the like may be optionally added at latest before use. In connection with this, additives for improving the conductivity (e.g. graphite powder, silver powder etc.) deserve to be mentioned. In case of use as a molding compound, the addition of anorganic and/or organic fillers such as (glass) fibers, minerals etc. must be especially considered.

The final curing of the poly(hetero)condensation products is effected either thermally or photochemically following the addition of suitable initiators. During this, the rings of the spiro-groups are opened and the organic network is synthesized in the process of a cationic polymerization. It was surprisingly discovered that during the course of this polymerization the volume of the poly(hetero)condensation products remained unchanged or changed only slightly. Depending upon the number of the spiro-groups, only a slight decrease of volume, or no change of volume, or even an increase of volume occurred, the decrease of volume becoming smaller with increase of the number of spiro-groups. Thus, by means of the spiro-silanes of the present invention it has become possible to obtain coatings, fillers and molding compounds as well as adhesive and sealing compounds based on silicic acid (hetero)condensation products which undergo no curing-shrinkage during the curing process.

However, it is also possible to add further components capable of undergoing ion polymerization and/or radical polymerization to the poly(hetero)condensation products before the final curing, i.e. before the polymerization. Compounds that are capable of undergoing radical polymerization and may be added are, for example, those having $C=C$ double bonds, such as acrylates or methacrylates, wherein the polymerization occurs through the $C=C$ double bonds. Compounds that are capable of undergoing ion polymerization and may be added contain, for example, ring systems that undergo cationic polymerization with ring opening, such as spiro-orthoesters, spiro-orthocarbonates, bicyclic spiro-orthoesters, mono or oligo epoxides or vinyl ethers. However, compounds capable of undergoing cation polymerization as well as radical polymerization may also be added, such as methacryloyl spiro-orthoesters. These undergo radical polymerization through the $C=C$ double bond and cation polymerization with ring opening. These systems have been described, for example, in Journal f. prakt. Chemie, Volume 330, No. 2, 1988, pages 316-318, or in Journal of Polymer Science, Part C, Polymer Letters, Volume 26, pages 517-520 (1988).

When the curing of the poly(hetero)condensation products is to be effected photochemically, cationic photo-initiators are added. Suitable photo-initiators are compounds that set free acids when irradiated, such as $C_6H_5-N_2BF_4$, $o-NO_2-C_6H_4-CH_2-O-SO_2CF_3$, triarylsulfonium salts of the general formulae (VII), (VIII) and (IX), wherein the residues Ar may be the same or different, and represent aryl or arylene, e.g. phenyl and phenylene, with $X^- = BF_4^-$, $AsF_6^-$, $PF_6^-$ or $SbF_6^-$.

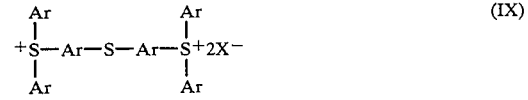

These photo-initiators may be obtained commercially, for example, triphenylsulfonium hexafluorophosphate as a 50% solution in propylene carbonate from Union Carbide under the tradename UVI-6990, or from Degussa under the tradename KI-85 (an initiator according to formula (IX) with Ar=phenyl or phenylene and $X^- = PF_6^-$ as a 50% solution in propylene carbonate). However, in principle all photo-initiators used for the polymerization of oxirane-containing molecules such as cycloaliphatic epoxides are suitable.

Under the effect of UV radiation, the triarylsulfonium salt is subjected to photolysis and a Broensted acid is formed which catalyses the ring-opening of the spiro-groups, wherein the poly(hetero)condensation product polymerizes.

In case the curing of the poly(hetero)condensation product is to be effected thermally, thermal initiators are added thereto. Suitable thermal initiators are, for example, $BF_3$ in the form of $BF_3.H_2NC_2H_5$, $ZnCl_2$, $TiCl_4$ or $SnCl_2$. Here too, all of the thermal initiators suitable for the polymerization of epoxy groups may be used.

The initiator may be added in usual amounts. Thus, for example, an initiator may be added in an amount of, for example, 0.5 to 5% by weight, especially 1 to 3% by weight, based on the mixture, to a mixture containing 30 to 50% by weight of solid matter (polycondensation product).

If further components containing reactive double bonds are used, such as the silanes according to the general formula (IV), in addition to the spiro-silanes of the present invention, for the preparation of the (hetero)polycondensation products, then a polymerization that may be thermally or photochemically initiated can also occur through these double bonds.

As photo-initiators, those commercially obtainable, for example, may be used. Examples of these are Iracure 184 (1-hydroxycyclohexyl phenyl ketone), Iracure 500 (1-hydroxycyclohexyl phenyl ketone/benzophenone), and other photoinitiators of the Iracure type obtainable from Ciba-Geigy; Darocure 1173, 1116, 1398, 1174 and 1020 (obtainable from Merck), benzophenone, 2-chlorothioxanthone, 2-methyl-thioxanthone, 2-isopropyl-thioxanthone, benzoin, 4,4'-dimethoxy-benzoin, and others.

Usable as thermal initiators are especially organic peroxides in the form of diacyl peroxides, peroxy dicarbonates, alkyl peresters, dialkyl peroxides, perketalene, ketone peroxides and alkyl hydroperoxides. Concrete and preferred examples of thermal initiators are dibenzoyl peroxide, t-butyl perbenzoate and azo-bisisobutyronitrile.

A varnish (poly(hetero)condensation product) on the basis of the spiro-silanes of the present invention and provided with an initiator may then bemused for coating substrates. Usual coating methods may be used to apply this coating, e.g. immersing, flooding, pouring, centrifuging, rolling, spraying, brush-painting, electrostatic spraying and electric immersion coating. It shall be mentioned here that the varnish need not necessarily contain a solvent. Especially when starting materials (silanes) having two alkoxy groups on the Si atom are used, work can be performed without the addition of solvents.

Before being cured, the coated varnish is preferably left to dry. Then, depending upon the kind of initiator, it may be thermally or photochemically cured in a manner known per se. Of course, combinations of curing methods are also possible.

In case the curing of the coated varnish is effected by irradiation, it may be of advantage to effect thermal curing after the radiation-curing, especially in order to remove any solvent still present or to involve further reactive groups in the curing process.

Although the poly(hetero)condensation products based on the spiro-silanes of the present invention already contain polymerizable groups, it maybe of advantage in certain cases to add further compounds (preferably of purely organic nature) having unsaturated groups to these condensates before or during their further processing (curing). Preferred examples of such compounds are acrylic acid and methacrylic acid as well as compounds derived therefrom, especially esters of preferably monovalent alcohols (e.g. $C_{1-4}$-alkanols), (meth-)acrylnitrile, styrene and mixtures thereof. These compounds may at the same time act as solvents or thinners in case the poly(hetero)condensation products are used to produce a coating varnish or lacquer.

The production of molded articles or molding compounds from poly(hetero)condensation products based on the spiro-silanes of the present invention may be effected with any of the methods used in this field, for example by injection molding, casting, extrusion, etc. The poly(hetero)condensation products based on the spiro-silanes of the present invention are also suitable for manufacturing composite materials (e.g. with glass fiber reinforcement).

A further possibility of applying the spiro-silanes of the present invention is provided by the production of hydrolytically condensable polymers. For this, the spiro-silanes of the present invention are polymerized either by themselves or together with other components capable of being subjected to radical and/or ion polymerization, wherein the final curing is then effected by hydrolytic condensation through the hydrolyzable groups of the spiro-silanes of the present invention and any other hydrolyzable components. In this case, the organic network is first synthesized by polymerization, and then the inorganic network is synthesized by hydrolytic condensation.

The production of the polymers is made by cation polymerization of one or more compounds containing 1,4,6-trioxaspiro-(4,4)-nonane and optionally other cation polymerizable compounds, and optionally by radical polymerization of one or more compounds capable of being radical-polymerized, using the effect of heat or electro-magnetic radiation, optionally in presence of one or more initiators and/or a solvent, and is characterized in that 5 to 100 mole-% based on the monomeric compounds, of the compounds containing 1,4,6-trioxaspiro-(4,4)-nonane are selected from the silanes of the present invention having the general formula (I).

However, it is also possible to add further components capable of being ion polymerised and/or radical polymerised to the spiro-silanes of the present invention before polymerization. Compounds capable of being radical polymerized and added are, for example, those with C=C double bonds, such as acrylates or methacrylates, wherein the polymerisation occurs through the C=C double bonds. Compounds capable of being ion polymerized and added contain, for example, ring systems capable of being cation polymerized with ring-opening, such as spiro-orthoesters, vinylethers, spiro-orthocarbonates, bicyclic spiro-orthoesters, mono or oligo epoxides. However, compounds may also be added that are capable of being cation polymerized as well as radical polymerised, such as methacryloyl-spiro-orthoesters. These can be radical polymerized through the C=C double bond and cation polymerized with ring-opening. These systems have been described, for example, in Journal f. prakt. Chemie, Volume 330, No. 2, 1988, pages 316–318, or in Journal of Polymer Science: Part C: Polymer Letters, Volume 26, pages 517–520 (1988).

In addition, further hydrolyzable and polymerizable compounds of silicon, optionally in precondensed form, may be added to the spiro-silanes of the present invention before polymerization, to then become involved in the polymerization. Silicon compounds of this kind are derived, for example, from epoxide-containing silanes and are therefore cation polymerizable and are used, amongst other purposes, for the production of the spiro-silanes of the present invention. These systems are already described in connection with the production of the spiro-silanes of the present invention.

However, silicon compounds may also be used that are derived, for example, from those of the general formula (IV) and that are capable of being radical polymerized. These systems have already been described in detail in connection with the production of the poly(-hetero)condensation products.

The polymerization is effected either thermally or photochemically following the addition of suitable initiators. For this, in the course of a cation polymerization, the rings of the spiro-groups are opened and, optionally, further ion polymerizable rings are opened and, optionally, a radical polymerization occurs by a linking of double bonds. During this the organic network, is synthesized. It was surprisingly discovered that the volume of the reaction mass does not change or changes only slightly during this polymerization. An only small decrease of volume, no change of volume, or even an increase of volume may be achieved in dependence upon the number of spiro-groups, wherein the reduction of volume becomes smaller with an increase of the number of spiro-groups.

When the polymerization is effected photochemically, cationic photo-initiators are added to the reaction mass. Suitable photo-initiators are compounds that set free acids during irradiation and that have already been described in detail in connection with the photochemical curing of the poly(hetero)condensation products.

When the polymerization is effected thermally, thermal initiators are added to the reaction mass. Suitable thermal initiators are, for example, $BF_3$ in the form of $BF_3 \cdot H_2NC_2H_5$, $ZnCl_2$, $TiCl_4$ or $SnCl_4$. Here too, all thermal initiators suitable for the polymerization of epoxide groups may be used.

If components having double bonds are added to the spiro-silanes of the present invention, a polymerization which may be thermally or photochemically initiated, may also occur through these double bonds.

As suitable photo-initiators for this, those commercially obtainable may be used, for example. Examples of these were already mentioned in connection with the curing of the poly(hetero) condensation products. Suitable thermal initiators may be chosen, in particular, from organic peroxides in the form of diacyl peroxides, peroxy dicarbonates, alkyl peresters, dialkyl peroxides, perketalenes, ketone peroxides and alkyl hydroperoxides. Concrete examples of these were also already mentioned in connection with the curing of the poly (hetero) condensation products.

The initiator may be added in usual amounts. Thus, for example, to a mixture containing 30 to 50% by weight of solid matter (polycondensate) the initiator may be added in an amount of, for example, 0.5 to 5% by weight, especially 1 to 3% by weight, based on the mixture.

The polymer obtained in this manner may now be hydrolytically condensed to synthesize the inorganic network, optionally in presence of further hydrolytically condensable compounds of silicon and, optionally, other elements selected from the group B, Al, P, Sn, Pb, the transition metals, the lanthanides and the actinides and/or precondensates derived from the above-named compounds, by the effect of water or dampness, optionally in presence of a catalyst and/or a solvent.

As distinct from the hydrolytic condensation of the spiro-silanes of the present invention, the hydrolytic condensation of the polymer may also be effected in an acid environment. The polymers contain hydrolyzable groups X, e.g. alkoxy groups, so that an inorganic network (Si—O—Si-units) may be synthesized.

Of the hydrolyzable compounds of silicon that may optionally be used, those of the general formula (III), optionally in precondensed form, are preferred. These systems have already been described in detail in connection with the production of the poly(hetero)condensation products, and concrete examples have been given.

Of the hydrolyzable aluminium compounds that may optionally be used, those having the general formula (V) are expecially preferred, and suitable hydrolyzable titanium or zirconium compounds, that may optionally be used, are those of the general formula (VI). These systems too were already discussed in detail in connection with the production of the poly (hetero) condensation products.

Further hydrolyzable compounds that may be added to the polymer are, for example, boron trihalides and boric acid esters, such as $BCl_3$, $B(OCH_3)_3$ and $B(OC_2H_5)_3$, tin tetrahalides and tin tetraalkoxides, such as $SnCl_4$ and $Sn(OCH_3)_4$, and vanadyl compounds such as $VOCl_3$ and $VO(OCH_3)_3$.

Here too, as already mentioned, the hydrolytic condensation may be effected in a manner usual in this field. The hydrolytic condensation may be effected in most cases by adding the necessary water directly at room temperature or with slight cooling, preferably with stirring and in presence of a hydrolysis and condensation catalyst, to the polymer to be hydrolysed that may be present either as such or dissolved in a suitable solvent.

In presence of the reactive compounds of Al, Ti or Zr it is as a rule recommendable to add the water stepwise. As a rule, the hydrolysis occurs at temperatures between $-20°$ and $130°$ C., preferably between $0°$ and $30°$ C. or the boiling point of the optionally used solvent, irrespective of the reactivity of the compounds present. As already indicated, the best manner of adding water depends, above all, upon the reactivity of the starting compounds used. Thus, for example, the dissolved polymer may be slowly added dropwise to excess into water, or the water may be added as one portion or in portions to the polymer that may optionally be dissolved. It may also be expedient not to add the water as such, but to introduce it into the reaction system by means of water-containing organic or inorganic systems.

The invention is further illustrated with working examples.

EXAMPLE 1

Preparation of 2-trimethoxysilyl-propylmethylether-1,4,6-trioxaspiro-(4,4)-nonane To 129 g (1.5 moles) γ-butyrolactone and 4.62 g boron trifluoride etherate ($BF_3$—$Et_2O$) present in 600 ml of dried $CH_2Cl_2$, a solution of 307 g (1.3 moles) 3-glycidyloxypropyl trimethoxysilane in 300 ml $CH_2Cl_2$ was added dropwise within one hour. After about two hours of stirring at room temperature, concentration is effected by means of a rotational evaporator and the residue is subjected to high vaccum distillation. Following a preliminary fraction, the desired spiro-silane is obtained as a colorless stable liquid at a temperature of about 125° C. (2.10$^{-2}$ mbar).

IR: (C—H) at about 2840-2969 cm$^{-1}$ (C—H, methoxy) at 2480 cm$^{-1}$

EXAMPLE 2

Hydrolytic condensation of 2-trimethoxysilyl-propyl-methylether-1,4,6-trioxaspiro-(4,4)-nonane To hydrolyze and condense the —Si(OCH$_3$)$_3$ groups, 20 mg triethylamine and 0.54 g (30 moles) H$_2$O are added dropwise to 6.54 g (20 moles) of the spiro-silane of Example 1. The mixture was stirred for about 20 h at room temperature. The resulting spiro-siloxane may be directly used for cation polymerization, on the one hand, and isolated following usual processing, on the other hand.

IR: (C—H, methoxy) at 2480 cm$^{-1}$ no longer present →hydrolysis has occurred (C=O, ester) at 1738 cm$^{-1}$ was not formed →spiro-group not split

EXAMPLE 3

Cation polymerisation of the spiro-siloxane from Example 2

The spiro-siloxane according to Example 2 is mixed with 2% starter (UVI-6990 from Union Carbide), coated onto KBr platelets, freed from all volatile components in vaccum, and irradiated with UV light (UV spot radiator "Blue Point" of the firm of Dr. K. Hönle), i.e. polymerization hardened (complete conversion after <1 min).

IR: (C=O, ester) at 1740 cm$^{-1}$ (intensive band) →complete conversion and thus polymerization of the spiro-group →polyester siloxane

EXAMPLE 4

Cation polymerisation of the spiro-siloxane from Example 2

The spiro-siloxane according to Example 2 is mixed with 2% starter (KI-85 from Degussa) and coated onto a glass specimen slide. The coating was produced by means of a film applicator frame having various slit widths (30 and 89 μm). The volatile components were drawn off in a vacuum drying cabinet (15 min, 40° C.), and the curing was effected by means of a UV radiator "UVALOC 1000" of the firm of Loctite.

Using the starters according to examples 3 and 4, colorless coatings were obtained after an irradiation duration of less than 1 minute.

Note: as 3-methoxy-groups are contained in the spiro-silane, the hydrolytic condensation yields a colorless plastic mass soluble in acetic ester. Using a spiro-silane having 2 alkoxy-groups, a liquid resin may expected.

I claim:

1. Hydrolyzable and polymerizable silanes of the general formula (I),

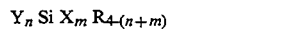

wherein the residues X, Y and R may be the same or different and are defined as follows:

R=alkyl, alkenyl, aryl, alkylaryl or arylalkyl,
X=hydrogen, halogen, hydroxyl, alkoxy, acyloxy, alkylcarbonyl, alkoxycarbonyl or NR'$_2$, with R'=hydrogen, alkyl or aryl,
Y=a substituent containing a substituted or unsubstituted 1,4,6-trioxaspiro-(4,4)-nonane residue,
n=1, 2 or 3,
m=1, 2 or 3, with n+m≦4.

2. Silanes according to claim 1, wherein Y is

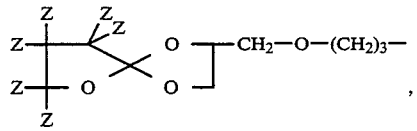

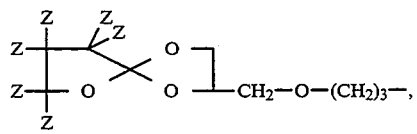

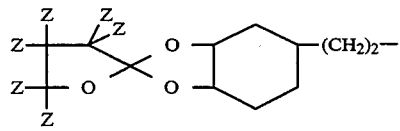

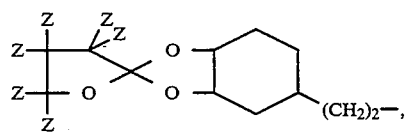

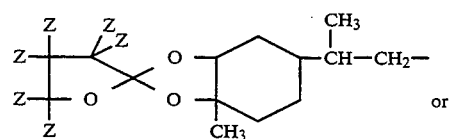

or

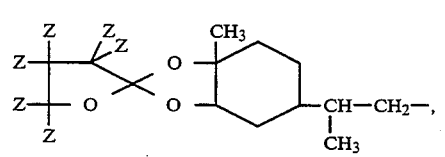

wherein the residues Z may be the same or different and represent hydrogen, hydroxyl, alkyl, alkenyl, aryl, alkylaryl, arylalkyl, alkylcarbonyl or alkoxycarbonyl.

3. 2-trimethoxysilyl-propylmethylethen-1,4,6-trioxaspiro-(4,4)-nonane.

4. A silane as defined in claim 1 that is:

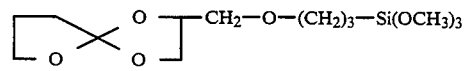

5. A silane as defined in claim 1 that is:

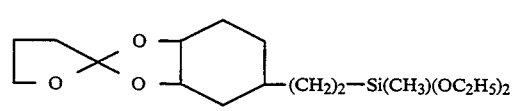

* * * * *